United States Patent
Saito et al.

[11] Patent Number: 5,831,132
[45] Date of Patent: Nov. 3, 1998

[54] PROCESS FOR PRODUCING OPTICALLY ACTIVE CARBINOLS

[75] Inventors: Kenji Saito, Hirakata; Norio Kometani, Kishiwada; Azusa Fujiwara, Kawachinagano; Yukio Yoneyoshi, Otsu; Gohfu Suzukamo, Suita, all of Japan

[73] Assignees: Sumika Fine Chemicals Company, Ltd.; Sumitomo Chemical Company, Ltd., both of Osaka, Japan

[21] Appl. No.: 549,399

[22] Filed: Oct. 27, 1995

[30] Foreign Application Priority Data

Oct. 28, 1994 [JP] Japan .................................. 6-289089
Dec. 20, 1994 [JP] Japan .................................. 6-335792
Jun. 22, 1995 [JP] Japan .................................. 7-156072
Jul. 12, 1995 [JP] Japan .................................. 7-176169
Jul. 12, 1995 [JP] Japan .................................. 7-176170

[51] Int. Cl.$^6$ .......................... C07C 33/46; C07C 27/00
[52] U.S. Cl. ........................................... 568/812; 568/814
[58] Field of Search ................................ 568/1, 705, 713, 568/880, 812, 814

[56] References Cited

FOREIGN PATENT DOCUMENTS 0178325  4/1986  European Pat. Off. .

OTHER PUBLICATIONS

Journal of The Chemical Society, Perkin Transactions 1, No. 8, Aug. 1989; Shinichi Itsuno et al.; "Asymmetric Reduction of Ketoxime O–Alkyl Ethers with Sodium Borohydride_Lewis Acid", pp. 1548–1549.

Journal of The Chemical Society, Perkin Transactions 1, 1985; Shinichi Itsuno et al.; "Asymmetric Synthesis Using Chirally Modified Borohydrides. Part 3. Enantioselective Reduction of Ketones and Oxime Ethers with Reagents Prepared from Borane and Chiral Amino Alcohols", pp. 2039–2044.

*Primary Examiner*—Gary Geist
*Assistant Examiner*—Karl J. Puttlitz, Jr.
*Attorney, Agent, or Firm*—Birch, Stewart, Kolasch & Birch, LLP

[57] ABSTRACT

The present invention relates to a process for producing optically active halomethyl phenyl carbinols of the formula (1), comprising reducing halomethyl phenyl ketones of the formula (2) using an asymmetric reducing agent obtained from boranes and optically active α-phenyl-substituted-β-amino alcohols of the formula (3) or optically active α-non-substituted-β-amino alcohols of the formula (4).

The present invention further relates to a process for producing optically active carbinols, comprising reacting a prochiral keytone with an asymmetric reducing agent obtained from optically active β-amino alcohols of the formula (5), a metal boron hydride and Lewis acid or lower dialkyl sulfuric acid. All of the formulas (1) to (5) are the same as shown in the specification.

15 Claims, No Drawings

PROCESS FOR PRODUCING OPTICALLY ACTIVE CARBINOLS

FIELD OF THE INVENTION

The present invention relates to a process for producing optically active carbinols. More particularly, it relates to a process for producing optically active carbinols, comprising reducing halomethyl phenyl ketones using an asymmetric reducing agent.

RELATED PRIOR ART

As a conventional process for producing optically active carbinols, for example, there has been known a process for producing optically active halomethyl phenyl carbinols, comprising reducing halomethyl phenyl ketones using an asymmetric reducing agent obtained from borane and optically active 2-amino-3-methyl-1,1-diphenylpentan-1-ol wherein hydrogen atoms on the α-position of β-amino alcohol are substituted by two phenyl groups.

In this process carbinols having a high optical purity, i.e. 83% ee carbinol and 96% ee carbinol can be obtained from bromomethyl phenyl ketone and chloromethyl phenyl ketone, respectively [e.g. J. Chem. Soc. PERKIN TRANS. I., 2039 (1985)].

However, when using the asymmetric reducing agent obtained from this β-amino alcohol, there arises such an industrial problem that, when the β-amino alcohol and objective carbinols are separated by the treatment with an acid, a salt which is slightly soluble to water is formed, thereby requiring a complicated post treatment step such as a filtering process.

It has also been known that, when methyl phenyl ketone is reduced using optically active 2-amino-3-methylbutan-1-ol containing no substituent at the α-position in place of the above optically active amino alcohol wherein hydrogen atoms on the α-position are substituted by two phenyl groups, the optical purity of the product is drastically decreased from 95% ee to 49% ee [e.g. J. Chem. Soc. PERKIN TRANS. I., 2039 (1985)]. Thus it has been believed that, when halomethyl phenyl ketone is reduced using optically active α-phenyl-substituted-β-amino alcohols containing only one phenyl group at the α-positions, a product having an drastically low optical purity is similarly obtained.

It has been known that, when bromomethyl phenyl ketone among halomethyl phenyl ketones is reduced, the optical purity is decreased by 10% or more in comparison with the case that chloromethyl phenyl ketone is reduced, as described above. It has been believed that, when bromomethyl phenyl ketone is reduced, a product having a lower optical purity is merely obtained.

On the other hand, in the production of optically active carbinols by asymmetric reduction reactions, there has been desired an industrially advantageous process using a reducing agent which is easily available in the industrial scale and is less expensive. In addition, there has been proposed a process using a metal boron hydride which is less expensive and is easily available, industrially, as a hydrogen resource, i.e. process for producing optically active carbinols, comprising reacting prochiral ketones with an asymmetric reducing agent obtained from 2-substituted oxazaborolidine containing a substituent on boron, metal boron hydride and acid (Japanese Laid-Open Patent Publication No 7-109231). However, according to this process, the optical purity of the resulting optically active carbinols is not necessarily satisfactory, and an improvement in this respect has been desired.

SUMMARY OF THE INVENTION

Under these circumstances, the present inventors have intensively studied asymmetric reducing agents obtained from β-amino alcohol in order to find an advantageous process for producing optically active carbinols. As a result, it has been surprisingly found that an asymmetric reducing agent obtained from reacting boranes with specific β-amino alcohol, i.e. α-phenyl-substituted-β-amino alcohols containing one phenyl group at the α-position, and makes the post treatment after the reaction simple and affords optically active halomethyl phenyl carbinols having a high optical purity. Various studies were conducted in this regard, thus such that present invention has been accomplished.

In addition, the present inventors have intensively studied the above issues in order to produce optically active alcohols having a higher optical purity using a metal boron hydride. As a result, it has been found that, when using a specific asymmetric reducing agent obtained from an optically active β-amino alcohol, metal boron hydride and Lewis acid or lower dialkyl sulfuric acid, optically active carbinols having a higher optical purity can be obtained. Various studies were conducted in this regard such that the present invention has been accomplished.

That is, the present invention provides an industrially excellent process for producing optically active halomethyl phenyl carbinols of the formula (1):

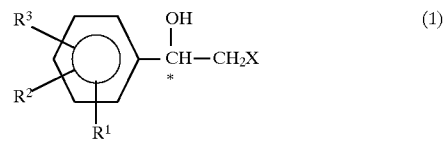

wherein X is a chlorine atom or bromine atom; $R^1$, $R^2$ and $R^3$ independently represent a hydrogen atom, halogen atom, a lower alkyl group or a lower alkoxy group; and * means an asymmetric carbon, comprising reducing halomethyl phenyl ketones of the formula (2):

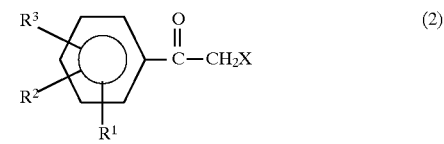

wherein X, $R^1$, $R^2$ and $R^3$ are the same as defined above, using an asymmetric reducing agent obtained from boranes and either optically active α-phenyl-substituted-β-amino alcohols of the formula (3):

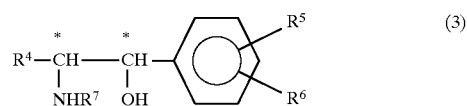

wherein $R^4$ represents an alkyl group having 1 to 6 carbon atoms; $R^5$ and $R^6$ independently represent a hydrogen atom, a lower alkyl group or a lower alkoxy group; $R^7$ represents a hydrogen atom, a lower alkyl group or an optionally substituted aralkyl group; and ψ means an asymmetric carbon, or optically active α-nonsubstituted- β-amino alcohols of the formula (4):

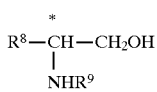

(4)

wherein $R^8$ represents an alkyl group having 1 to 6 carbon atoms, an aryl group which is optionally substituted with a lower alkyl group or a lower alkoxy group, or an aralkyl group which is optionally substituted with a lower alkyl group or a lower alkoxy group; $R^9$ represents a hydrogen atom, a lower alkyl group or an optionally substituted aralkyl group, or $R^9$ and Re bond together to represent a lower alkylene group; and * means an asymmetric carbon.

In addition, the present invention also provides an industrially excellent process for producing optically active carbinols, comprising reacting a prochiral ketone with an asymmetric reducing agent obtained from optically active β-amino alcohols of the formula (5):

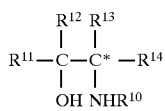

(5)

wherein $R^{10}$ represents a hydrogen atom, a lower alkyl group or an optionally substituted aralkyl group; $R^{11}$, $R^{12}$, $R^{13}$ and $R^{14}$ independently represent a hydrogen atom, a lower alkyl group, an optionally substituted aryl group or an optionally substituted aralkyl group, $R^{13}$ and $R^{14}$ are not the same, $R^{10}$ and $R^{14}$ may bond together to represent a lower alkylene group and $R^{12}$ and $R^{13}$ may bond together to represent an optionally substituted lower alkylene group; and * means an asymmetric carbon, a metal boron hydride and Lewis acid or lower dialkyl sulfuric acid.

DETAILED DESCRIPTION

Hereinafter, the present invention will be described in detail.

Process for producing optically active halomethyl phenyl carbinols (1) using an asymmetric reducing agent obtained from boranes and β-amino alcohols (3 or 4)

X in the halomethyl phenyl ketones represented by the formula (2) represents a chlorine atom or a bromine atom, preferably bromine atom.

Examples of $R^1$, $R^2$ and $R^3$ include hydrogen atom; halogen atoms such as fluorine, chlorine, bromine, etc.; lower alkyl groups such as methyl, ethyl, n-propyl, i-propyl, n-butyl, i-butyl, sec-butyl, t-butyl, etc.; lower alkoxy groups such as methoxy, ethoxy, propoxy, butoxy, etc..

Typical examples of the halomethyl phenyl ketones (2) wherein X is a bromine atom include 2-bromoacetophenone,
2-bromo-3'-chloroacetophenone,
2-bromo-3'-bromoacetophenone,
2-bromo-3'-fluoroacetophenone,
2-bromo-3'-methylacetophenone,
2-bromo-3'-ethylacetophenone,
2-bromo-3'-propylacetophenone,
2-bromo-3'-butylacetophenone,
2-bromo-3'-methoxyacetophenone,
2-bromo-3'-ethoxyacetophenone,
2-bromo-3'-propoxyacetophenone,
2-bromo-3'-butoxyacetophenone,
2-bromo-4'-chloroacetophenone,
2-bromo-4'-bromoacetophenone,
2-bromo-4'-fluoroacetophenone,
2-bromo-4'-methylacetophenone,
2-bromo-4'-ethylacetophenone,
2-bromo-4'-propylacetophenone,
2-bromo-4'-butylacetophenone,
2-bromo-4'-methoxyacetophenone,
2-bromo-4'-ethoxyacetophenone,
2-bromo-4'-propoxyacetophenone,
2-bromo-4'-butoxyacetophenone,
2-bromo-2'-chloroacetophenone,
2-bromo-2'-bromoacetophenone,
2-bromo-2'-fluoroacetophenone,
2-bromo-2'-methylacetophenone,
2-bromo-2'-ethylacetophenone,
2-bromo-2'-propylacetophenone,
2-bromo-2'-butylacetophenone,
2-bromo-2'-methoxyacetophenone,
2-bromo-2'-ethoxyacetophenone,
2-bromo-2'-propoxyacetophenone,
2-bromo-2'-butoxyacetophenone,
2-bromo-2'-chloro-3'-methoxyacetophenone,
2-bromo-2'-bromo-3'-methoxyacetophenone,
2-bromo-2'-fluoro-3'-methoxyacetophenone,
2-bromo-3'-methoxy-2'-methylacetophenone,
2-bromo-2',3'-dimethoxy-acetophenone,
2-bromo-2'-ethoxy-3'-methoxyacetophenone,
2-bromo-2',3'-dichloroacetophenone,
2-bromo-2'-bromo-3'-chloroacetophenone,
2-bromo-3'-chloro-2-fluoroacetophenone,
2-bromo-3'-chloro-2'-fluoroacetophenone,
2-bromo-3'-chloro-2'-methylacetophenone,
2-bromo-3'-chloro-2'-methoxyacetophenone,
2-bromo-3'-chloro-2'-ethoxyacetophenone,
2-bromo-3'-bromo-4'-chloroacetophenone,
2-bromo-2',4'-dibromoacetophenone,
2-bromo-2'-bromo-4'-fluoroacetophenone,
2-bromo-2'-bromo-4'-methylacetophenone,
2-bromo-2'-bromo-4'-methoxyacetophenone,
2-bromo-4'-chloro-2'-fluoroacetophenone,
2-bromo-2',4'-difluoroacetophenone,
2-bromo-4'-bromo-2'-fluoroacetophenone,
2-bromo-2'-fluoro-4'-methylacetophenone,
2-bromo-2'-fluoro-4'-methoxyacetophenone,
2-bromo-4'-ethoxy-2'-fluoroacetophenone,
2-bromo-4'-chloro-2'-ethoxyacetophenone,
2-bromo-4'-bromo-2'-ethoxyacetophenone,
2-bromo-4'-fluoro-2'-ethoxy-acetophenone,
2-bromo-4'-methyl-2'-ethoxyacetophenone,
2-bromo-4'-methoxy-2'-ethoxyacetophenone,
2-bromo-4',2'-diethoxyacetophenone,
2-bromo-4'-chloro-3'-thoxyacetophenone,
2-bromo-4'-bromo-3'-ethoxyacetophenone,
2-bromo-4'-fluoro-3'-ethoxyacetophenone,
2-bromo-3'-ethoxy-4'-methylacetophenone,
2-bromo-3'-ethoxy-4'-methoxyacetophenone,
2-bromo-3',4'-diethoxyacetophenone,
2-bromo-5'-bromo-3'-chloroacetophenone,
2-bromo-3,5'-dibromoacetophenone,
2-bromo-5'-bromo-3'-fluoroacetophenone,
2-bromo-5'-bromo-3'-methylacetophenone,
2-bromo-5'-bromo-3'-methoxyacetophenone,
2-bromo-5'-bromo-3'-ethoxyacetophenone,
2-bromo-3'-chloro-5'-ethoxyacetophenone,
2-bromo-3'-bromo-5'-ethoxyacetophenone,
2-bromo-5'-ethoxy-3'-fluoroacetophenone,
2-bromo-5'-ethoxy-3'-methylacetophenone,
2-bromo-5'-ethoxy-3'-methoxyacetophenone,
2-bromo-3',5'-dimethoxyacetophenone,
2-bromo-3',5'-diethoxyacetophenone,
2-bromo-3',5'-dichloroacetophenone,
2-bromo-3',5'-difluoroacetophenone,
2-bromo-2',6'-dichloroacetophenone, 2-bromo-2',4',6'-trichloroacetophenone,
2-bromo-3',4',5'-trichloroacetophenone, etc.

When X is a chlorine atom, for example, compounds analogous to the above 2-bromo-substituted compounds may be used wherein 2-chloro replaces 2-bromo in the above compounds.

Halomethyl phenyl ketones (2) can be produced, for example, by reacting the corresponding methyl phenyl ketones (6), wherein $R^1$, $R^2$ and $R^3$ are as defined above, with sulfuryl chloride or bromine.

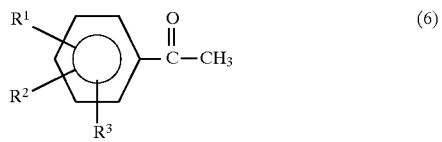

For example, it is preferred to use methanol as the solvent when methyl phenyl ketones (6) are reacted with bromine, thereby producing the objective bromomethyl phenyl ketones (7), wherein $R^1$, $R^2$ and $R^3$ are as defined above, in a high yield without forming by-product.

When using ethanol, propanol, etc. as the solvent, a large amount of by-products such as dibromomethyl phenyl ketone are formed, which results in considerable decrease in yield of bromomethyl phenyl ketones (7)

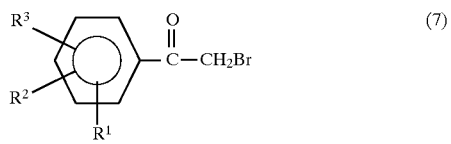

Anhydrous methanol is normally used, and the amount is normally 0.5 to 20 parts by weight, preferably 1.5 to 10 parts by weight per one part of methyl phenyl ketones (6). The reaction between methyl phenyl ketones (6) and bromine is normally carried out by adding bromine to a methanol solution of methyl phenyl ketones (6). Bromine 5 is normally used in an amount of 0.5 to 1.2 mole, preferably 0.8 to 0.99 mole per one mole of methyl phenyl ketones (6).

The reaction is normally carried out by (i) adding bromine at 20° to 60° C., preferably 30° to 45° C., over about 0.1 to 5 hours, (ii) stirring for about 0.1 to 3 hours, (iii) adding water in the same amount as that of methanol, and (iv) followed by stirring for about 0.1 to 3 hours.

The objective product is taken out of the reaction mass by adding water in at least half amount of methyl phenyl ketones (6) to deposit the objective product as a solid, followed by filtering and washing. The product can be optionally purified by recrystallizing from an organic solvent such as hexane, heptane, i-propanol, etc..

The present invention is characterized in that the above halomethyl phenyl ketones (2) are reduced with an asymmetric reducing agent obtained from optically active α-phenyl-substituted-β-amino alcohols (3) or optically active α-nonsubstituted-β-amino alcohols (4) and boranes.

Examples of $R^4$ in the optically active α-phenyl-substituted-β-amino alcohols (3) include alkyl groups having 1 to 6 carbon atoms, such as methyl, ethyl, n-propyl, i-propyl, n-butyl, i-butyl, sec-butyl, t-butyl, pentyl, hexyl, cyclohexyl, etc.

Examples of $R^5$ and $R^6$ include lower alkyl groups such as methyl, ethyl, n-propyl, i-propyl, n-butyl, i-butyl, sec-butyl, t-butyl, etc.; lower alkoxy groups such as methoxy, ethoxy, propoxy, butoxy, etc.

Examples of $R^7$ include a hydrogen atom; lower alkyl groups such as methyl, ethyl, n-propyl, i-propyl, n-butyl, i-butyl, sec-butyl, t-butyl, etc.; aralkyl groups which optionally contain a substituent (e.g. $C_1$–$C_4$ alkyl, halogen, $C_1$ –$C_4$ alkoxy, etc.), such as benzyl, phenylethyl, p-methylbenzyl, etc.

Examples of $R_8$ in the optically active α-non-substituted-β-amino alcohols (4) include alkyl groups having 1 to 6 carbon atoms, such as methyl, ethyl, n-propyl, i-propyl, n-butyl, i-butyl, sec-butyl, t-butyl, pentyl, hexyl, etc.; aryl groups which are optionally substituted with a lower alkyl group (having 1 to 4 carbon atoms, normally) or a lower alkoxy group (having 1 to 4 carbon atoms, normally), such as phenyl, naphthyl, p-methylphenyl, p-methoxyphenyl, etc.; aralkyl groups which are optionally substituted with a lower alkyl group (having 1 to 4 carbon atoms, normally) or a lower alkoxy group (having 1 to 4 carbon atoms, normally), such as benzyl, phenylethyl, p-methylbenzyl, p-methoxybenzyl, etc.

Examples of $R^9$ include a hydrogen atom; lower alkyl groups such as methyl, ethyl, n-propyl, i-propyl, n-butyl, i-butyl, sec-butyl, t-butyl, etc.; aralkyl groups which are optionally substituted with a lower alkyl group (having 1 to 4 carbon atoms, normally) or a ) lower alkoxy group (having 1 to 4 carbon atoms, normally), such as benzyl, phenylethyl, p-methylbenzyl, p-methoxybenzyl, etc.

In addition, $R^8$ and $R^9$ can bond together to represent lower alkylene groups such as methylene, dimethylene, trimethylene, tetramethylene, etc.

Typical examples of the optically active α-phenyl-substituted-β-amino alcohols (3) include norephedrine, 2-amino-1-(2-methoxyphenyl)-1-propanol, 2-amino-1-(2-ethoxyphenyl)-1-propanol, 2-amino-1 -(2-propoxyphenyl)-1-propanol, 2-amino-1-(2-methylphenyl)-1-propanol, 2-amino-1-(2,5-dimethylphenyl)-1-propanol, 2-amino-1-(2,5-dimethoxyphenyl)-1-propanol, 2-amino-1-(2,5-diethoxyphenyl)-1-propanol, 2-amino-1-(2,5-dipropoxyphenyl)-1-propanol, 2-amino-1-(2-methoxy-5-methylphenyl)-1-propanol, 2-amino-1-(4-methoxy-2-methylphenyl)-1-propanol, 2-amino-1-(2-ethoxy-5-methylphenyl)-1-propanol, 2-amino-1-(2,4-dimethylphenyl)-1-propanol, 2-amino-1-(2,4,6-trimethylphenyl)-1-propanol, 1-phenyl-2-amino-1-butanol, 1-phenyl-2-amino-1-pentanol, 1-phenyl-2-amino-1-hexanol, which are optically active, and N-alkyl- or N-aralkyl-substituted substances thereof.

Typical examples of the optically active α-non-substituted-β-amino alcohols (4) include valinol, leucinol, alaninol, phenylalaninol, phenylglycinol, prolinol, 2-azetidine methanol, 2-aziridine methanol, 2-pyrrolidine methanol, which are optically active, and N-alkyl- or N-aralkyl-substituted substances thereof.

The amount of the optically active α-phenyl-substituted-β-amino alcohols (3) to be used is normally 0.01 to 0.8 mole,.preferably 0.02 to 0.25 mole, per one mole of the halomethyl phenyl ketones (2). The amount of the optically active α-non-substituted-β-amino alcohols (4) to be used is normally 0.01 to 0.8 mole, preferably 0.02 to 0.25 mole, per one mole of the halomethyl phenyl ketones (2).

Examples of the boranes include diborane, tetraborane, hexaborane, tetrahydrofuran-borane complex, dimethyl sulfide-borane complex, alkyl borane, catecol-borane complex, thioxane-borane complex, etc.

The amount of the boranes to be used is normally 0.8 to 2 mole (in terms of boron), preferably 1.0 to 1.5 mole, per one mole of the optically active α-phenyl-substituted-β-amino alcohols (3) or of the optically active α-non-substituted-β-amino alcohols (4), and the amount is in a ranges of 0.3 to 2 mole (in terms of boron), preferably 0.5 to 1.5 mole, per one mole of the halomethyl phenyl ketones (2).

The production of the asymmetric reducing agent by the reaction between the optically active α-phenyl-substituted-β-amino alcohols (3) or optically active α-non-substituted-β-amino alcohols (4) and boranes is normally carried out in a solvent.

Examples of the solvent include ethers such as tetrahydrofuran, 1,3-dioxane, 1,4-dioxane, 1,3-dioxolane, thioxane, ethylene glycol dimethyl ether, diethylene glycol dimethyl ether, methyl-t-butyl ether, etc.; aromatic solvents such as benzene, toluene, xylene, chlorobenzene, etc.; hydrocarbons such as hexane, heptane, cyclohexane, etc.; halogenated hydrocarbons such as methylene chloride, ethylene chloride, carbon tetrachloride, etc.; and a mixture thereof.

The amount of the solvent is normally 0.5 to 50 parts by weight per one part of the optically active α-phenyl-substituted-β-amino alcohols (3) or of the optically active α-non-substituted-β-amino alcohols (4). The reaction temperature is normally −20° to 80° C., preferably 0° to 60° C. The reaction time varies depending on the reaction temperature, but is normally about 10 minutes to 3 hours.

In the reduction of the halomethyl phenyl ketones (2), the asymmetric reducing agent to be obtained from the optically active α-phenyl-substituted-β-amino alcohols (3) or optically active α-non-substituted-β-amino alcohols (4) and boranes may be used after isolation, but is normally used without isolation.

The reaction is normally carried out by adding halomethyl phenyl ketones (2) or a mixture of halomethyl phenyl ketones and a solvent to a mixture of the asymmetric reducing agent and solvent, or adding a mixture of the asymmetric reducing agent and solvent to a mixture of halomethyl phenyl ketones (2) and a solvent.

As the solvent for halomethyl phenyl ketones (2), for example, there are the same solvents as those described in the preparation process of the asymmetric reducing agent. The amount of the solvent is normally 0.1 to 20 parts by weight, preferably 1 to 18 parts by weight, per one mole of the halomethyl phenyl ketones (2).

The reaction temperature is normally about −76° to 100° C., preferably about 10° to 80° C. The reaction time varies depending on the temperature, amount of the boranes, optically active α-phenyl-substituted-β-amino alcohols (3) or optically active α-non-substituted-β-amino alcohols (4), etc., but is normally about 1 to 10 hours.

The objective optically active halomethyl phenyl carbinols (1) can be easily isolated, for example, by adding an acid (e.g. hydrochloric acid, etc.) to the reaction mass to decompose the reducing agent, optionally distilling off the solvent, adding an extraction solvent (e.g. toluene, etc.) and an aqueous acid solution (e.g. hydrochloric acid, etc.) to remove an acid salt of the optically active α-phenyl-substituted-β-amino alcohols (3) or optically active α-non-substituted-β-amino alcohols (4) to the aqueous layer and distilling off the solvent of the organic layer separated.

In addition, the optically active α-phenyl-substituted-β-amino alcohols (3) or optically active α-non-substituted-β-amino alcohols (4) can be recovered by alkalifying the acid salt thereof removed to the aqueous layer, extracting with a solvent (e.g. toluene, etc.) and distilling off the solvent.

The isolated optically active halomethyl phenyl carbinols (1) can also be further purified by subjecting to purification means such as distillation, various chromatographies, etc.

Thus, the objective optically active halomethyl phenyl carbinols (1) have been obtained. Examples of the compounds include bromomethyl phenyl carbinol, bromomethyl-3'-chlorophenyl carbinol, bromomethyl-3'-bromophenyl carbinol, bromomethyl-3'-fluorophenyl carbinol, bromomethyl-3'-methylphenyl carbinol, bromomethyl-3'-methoxyphenyl carbinol, bromomethyl-3'-ethoxyphenyl carbinol, bromomethyl-4'-chlorophenyl carbinol, bromomethyl-4'-bromophenyl carbinol, bromomethyl-4'-fluorophenyl carbinol, bromomethyl-4'-methlphenyl carbinol, bromomethyl-4'-methoxyphenyl carbinol, bromomethyl-4'-ethoxyphenyl carbinol, bromomethyl-2'-chlorophenyl carbinol, bromomethyl-2'-bromophenyl carbinol, bromomethyl-2'-fluorophenyl carbinol, bromomethyl-2'-methylphenyl carbinol, bromomethyl-2'-methoxyphenyl carbinol, bromomethyl-2'-ethoxyphenyl carbinol, bromomethyl-3'-chloro-2'-methoxyphenyl carbinol, bromomethyl-3'-bromo-2'-methoxyphenyl carbinol, bromomethyl-3'-fluoro-2'-methoxyphenyl carbinol, bromomethyl-2'-fluoro-3'-methylphenyl carbinol, bromomethyl-2',3'-dimethoxyphenyl carbinol, bromomethyl-3'-ethoxy-2'-methoxyphenyl carbinol, bromomethyl-2',4'-dichlorophenyl carbinol, bromomethyl-4'-bromo-2'-chlorophenyl carbinol, bromomethyl-2'-chloro-4'-fluorophenyl carbinol, bromomethyl-2'-chloro-4'-methoxyphenyl carbinol, bromomethyl-2'-chloro-4'-methylphenyl carbinol, bromomethyl-2'-chloro-4'-ethoxyphenyl carbinol, bromomethyl-3'-chloro-5'-ethoxyphenyl carbinol, bromomethyl-3'-bromo-5'-ethoxyphenyl carbinol, bromomethyl-5'-ethoxy-3'-fluorophenyl carbinol, bromomethyl-5'-ethoxy-3'-methylphenyl carbinol, bromomethyl-5'-ethoxy-3'-methoxyphenyl carbinol, bromomethyl-3',5'-diethoxyphenyl carbinol, bromomethyl-3',5'-dichlorophenyl carbinol, bromomethyl-3',5'-dibromophenyl carbinol, bromomethyl-3',5'-difluorophenyl carbinol, bromomethyl-2',4',6'-trifluorophenyl carbinol, bromomethyl-2',4',6'-trichlorophenyl carbinol, bromomethyl-2',4',6'-tribromophenyl carbinol, bromomethyl-3',4'-dichlorophenyl carbinol, bromomethyl-3',4'-dibromophenyl carbinol, bromomethyl-3',4'-difluorophenyl carbinol, etc., which are optically active.

According to the present invention, there can be produced optically active halomethyl phenyl carbinols (1) which are useful as synthetic intermediates of a remedy for diabetes, a remedy for hyperglycemia, a preventive/remedy for obesity, etc. in high optical purity, from halomethyl phenyl ketoens (2) by using an asymmetric reducing agent obtained from boranes and specific β-amino alcohols, such as α-phenyl-substituted-β-amino alcohols (3) containing one α-phenyl group at the β-position or α-non-substituted-β-amino alcohols (4) containing no substituent at the α-position.

The post treatment after the reaction is simple and, therefore, the present invention is also industrially advantageous in this respect.

Process for producing optically active carbinols using a asymmetric reducing agent obtained from optically active β-amino alcohol (5), metal boron hydride and Lewis acid or lower-dialkylsulfuric acid Examples of $R^{10}$ in the optically active β-amino alcohols of the formula (5) to be used in the present invention include a hydrogen atom; lower alkyl groups such as methyl, ethyl, n-propyl, i-propyl, n-butyl, i-butyl, sec-butyl, t-butyl, pentyl, etc.; aralkyl groups which optionally contain a substituent such as lower alkyl group (having 1 to 4 carbon atoms, normally) or lower alkoxy group (having 1 to 4 carbon atoms, normally), such as benzyl, phenethyl, methylbenzyl, etc.

Examples of $R^{11}$, $R^{12}$, $R^{13}$ and $R^{14}$ include hydrogen atoms; lower alkyl groups such as methyl, ethyl, n-propyl, i-propyl, n-butyl, i-butyl, sec-butyl, t-butyl, pentyl, etc.;

phenyl; phenyl substituted with the lower alkyl group (having 1 to 5 carbon atoms, normally) as that described above; phenyl substituted with a lower alkoxy group (having 1 to 5 carbon atoms, normally) such as methoxy, ethoxy, propoxy, butoxy, pentoxy, etc.; aryl group which optionally contains a substituent (e.g. $C_1$–$C_5$ alkyl, $C_1$–$C_5$ alkoxy, halogen, etc.), such as 1-naphthyl, 2-naphthyl, etc.; aralkyl groups which optionally contain a substituent (e.g. lower alkyl group having 1 to 5 carbon atoms, lower alkoxy group having 1 to 5 carbon atoms, normally), such as benzyl, phenethyl, methylbenzyl, etc.; provided that $R^{13}$ and $R^{14}$ are not the same.

Examples of the lower alkylene group formed by bonding $R^{10}$ and $R^{14}$ to each other include methylene, dimethylene, trimethylene, tetramethylene, etc. Examples of the lower alkylene group formed by bonding $R^{12}$ and $R^{13}$ to each other include trimethylene, tetramethylene, 1,2,2-trimethyl-1,3-cyclopentylene, etc.

Typical examples of the optically active β-amino alcohol (5) include norephedrine, ephedrine, 2-amino-1-(2,5-dimethylphenyl)-1-propanol, 2-amino-1-(2,5-dimethoxyphenyl)--propanol, 2-amino-1-(2,5-diethoxyphenyl)-1-propanol, 2-amino-1-(2,5-dipropoxyphenyl)-1-propanol, 2-amino-1-(2-methoxyphenyl)-1-propanol, 2-amino-1-(2-ethoxyphenyl)-1-propanol, 2-amino-1-(2-propoxyphenyl)-1-propanol, 2-amino-1-(2-methylphenyl)1-propanol, 2-amino-1-(2-methoxy-5-methylphenyl)-1-propanol, 2-amino-1-(4-methoxy-2-methylphenyl)-1-propanol, 2-amino-1-(2-ethoxy-5-methyl-phenyl)-1-propanol, 2-amino-1-(2,4-dimethylphenyl)-1-propanol, 2-amino-1-(2,4,6-trimethylphenyl)-1-propanol, 2-amino-1-(1-naphthyl)-1-propanol, 2-amino-1-(2-naphthyl)-1-propanol, 2-amino-1,2-diphenylethanol, 2-amino-1,1-diphenyl-3-methyl-1-propanol, 2-amino-1,1-diphenyl-4-methyl-1-butanol, 2-amino-1,1-diphenyl-3-methyl-1-propanol, 2-amino-1,1-diphenyl-1-propanol, 2-amino-1,1,3-triphenyl-1-propanol, 2-amino-1,1,2-triphenyl-1-ethanol, 2-amino-3-methyl-1-butanol, 2-amino-4-methyl-1-pentanol, 2-amino-1-propanol, 2-amino-3-phenyl-1-propanol, 2-amino-2-phenyl-1-ethanol, 2-aminocyclohexanol, 3-aminoborneol, etc., which are optically active, and lower N-alkyl- or N-aralkyl-substituted substances thereof, 2-pyrrolidine methanol, α,α-diphenyl-2-pyrrolidine methanol, 2-piperidene methanol, α,α-diphenyl-2-azilidene methanol, 2-azetidine methanol, α,α-diphenyl-2-azetidiene methanol, etc., which are also optically active.

The amount of the optically active β-amino alcohol(5) is normally 0.01 to 0.5 mole, preferably 0.02 to 0.4 mole per one mole of prochiral ketones.

Examples of the metal boron hydride to be used in the present invention include lithium boron hydride, sodium boron hydride, potassium boron hydride, zinc boron hydride, etc.. Among them, sodium boron hydride is normally used.

The amount of the metal boron hydride is normally 0.3 to 3 mole (in terms of borane), preferably 0.5 to 2 mole, per one mole of prochiral ketones.

Examples of the Lewis acid to be used in the present invention include zinc chloride, boron trifluoride, aluminum chloride, aluminum bromide, tin tetrachloride, tin dichloride or a mixture thereof.

Examples of the lower dialkyl sulfuric acid are those having 2 to 8 carbon atoms, such as dimethyl sulfuric acid, diethyl sulfuric acid, etc.

The amount of the Lewis acid is normally 0.5 to 2.5 chemical equivalents, preferably 0.8 to 2.2 chemical equivalents, per one chemical equivalent of the metal boron hydride. The amount of the lower dialkyl sulfuric acid is normally 0.9 to 1.1 mole, preferably 0.95 to 1.05 mole , per one mole of the metal boron hydride.

The reaction is normally carried out in a solvent. Examples of the solvent include ethers such as dioxane, tetrahydrofuran, diglyme, triglyme, 1,3-dioxolane, etc.; sulfides such as dimethyl sulfide, diethyl sulfide, etc.; or a mixture thereof; and a mixture of the above solvent or a mixture thereof and hydrocarbons such as benzene, toluene, xylene, chlorobenzene, 1,2-dichloroethane, etc. The amount of the solvent is normally 1 to 50 parts by weight per one part by weight of prochiral ketones.

The asymmetric reducing-agent can be prepared by adding Lewis acid or lower dialkyl sulfuric acid to a mixture of the optically active β-amino alcohol (5), metal boron hydride and solvent, or adding the optically active β-amino alcohol (5) after adding Lewis acid or lower dialkyl sulfuric acid to a mixture of the metal boron hydride and solvent. In this case, Lewis acid or lower dialkyl sulfuric acid may be added as a mixture with the solvent. The preparation temperature of the asymmetric reducing agent is normally −20° to 100° C., preferably 0° to 80° C. It is preferred to maintain at the same temperature with stirring for about 0.1 to 10 hours after adding Lewis acid or lower dialkyl sulfuric acid.

Reduction of the prochiral ketones are performed by treating the asymmetric reducing agent with the prochiral ketones, and it is preferred to add the prochiral ketones to the asymmetric reducing agent. In this case, the prochiral ketones can also be added after mixing with a solvent.

The reduction temperature is normally not higher than 150° C., preferably in a range of about −20° to 100° C., more preferably in a range of about 0° to 80°C.

The time to add the prochiral ketones is normally about 0.1 to 20 hours. It is preferred to maintain at the same temperature with stirring for about 0.1 to 10 hours after adding the prochiral ketones.

The proceeding of the reaction can be confirmed by analytical means such as gas chromatography, etc.

Examples of the prochiral ketones include prochiral ketones represented by the formula (8):

$$R^{15}—CO—R^{16} \qquad (8)$$

wherein $R^{15}$ and $R^{16}$ are different and represent an optionally substituted alkyl group, an optionally substituted aryl group or an optionally substituted aralkyl group. Examples of the optically active carbinols to be obtained by applying the prochiral ketones (8) to the reaction of the present invention include compounds represented by the formula (9)

$$\underset{*}{R^{15}—\underset{|}{\overset{OH}{C}H}—R^{16}} \qquad (9)$$

wherein $R^{15}$ and $R^{16}$ are as defined above; and * is an asymmetric carbon.

Examples of the alkyl group in $R^{15}$ and $R^{16}$ include alkyl groups having 1 to 6 carbon atoms, which are optionally substituted with a halogen, such as methyl, ethyl, propyl, butyl, pentyl, cyclopentyl, hexyl, cyclohexyl, chloromethyl, bromomethyl, dichloromethyl, trichloromethyl, tribromomethyl, trifluoromethyl, 2-chloroethyl, 3-chloropropyl, 4-chlorobutyl, etc. Examples of the aryl group include phenyl, substituted-phenyl, 1-naphthyl, 2-naphthyl, 2-pyridyl, 3-pyridyl, etc. Examples of the substituted-phenyl include halogen-substituted phenyl such as o-, m- or p-chlorophenyl, o-, m- or p-bromophenyl, 2,3-, 2,4 -, 2,5-, 2,6-, 3,4- and 3,5-dichlorophenyl, etc.; lower alkyl (having 1 to 4 carbon atoms, normally)-substituted phenyl such as o-, m- or p-methylphenyl, o-, m- or p-ethylphenyl, o-, m- or p-propylphenyl, o-, m- or p-butylphenyl, 2,3-, 2,4-, 2,5-, 2,6-, 3,4- and 3,5-dimethylphenyl, etc.; lower alkoxy (having 1 to 4 carbon atoms, normally)-substituted phenyl such as o-, m- or p-methoxyphenyl, o-, m- or p-ethoxyphenyl, o-, m- or p-propoxyphenyl, etc.; benzyloxy-substituted phenyl such as o-, m- or p-benzyloxyphenyl, etc.; cyano-substituted phenyl such as o-, m- or p-cyanophenyl, etc.

Examples of the aralkyl group include aralkyl groups which optionally contains a substituent having 7 to 11 carbon atoms, such as benzyl, o-, m- and p-tolylmethyl, o-, m- and p-ethylbenzyl, o-, m- and p-methoxybenzyl, o-, m- and p-ethoxybenzyl, etc.

Typical examples of the prochiral ketones (8) include acetophenone, propiophenone, butyrophenone, 1-acetonaphthone, 2-acetonaphthone, o-methoxyacetophenone, o-ethoxyacetophenone, o-propoxyacetophenone, o-benzyloxyacetophenone, p-cyanoacetophenone, phenylbenzyl ketone, phenyl(o-tolylmethyl) ketone, phenyl(p-tolylmethyl) ketone, phenyl(m-tolylmethyl) ketone, 2-butanone, 2-pentanone, 2-hexanone, 2-heptanone, 2-octanone, cyclohexylmethyl ketone, cyclohexylbenzyl ketone, 2-chloroacetophenone, 2-bromoacetophenone,
2-bromo-3'-chloroacetophenone,
2-chloro-3'-chloroacetophenone,
2-bromo-3'-bromoacetophenone;
2-bromo-3'-fluoroacetophenone,
2-bromo-3'-methylacetophenone,
2-bromo-3'-ethylacetophenone,
2-bromo-3'-propylacetophenone,
2-bromo-3'-butylacetophenone,
2-bromo-3'-methoxyacetophenone,
2-bromo-3'-ethoxyacetophenone,
2-bromo-3'-propoxyacetophenone,
2-bromo-3'-butoxyacetophenone,
2-bromo-4'-chloroacetophenone,
2-bromo-4'-bromoacetophenone,
2-bromo-4'-fluoroacetophenone,
2-bromo-4'-methylacetophenone,
2-bromo-4'-ethylacetophenone,
2-bromo-4'-propylacetophenone,
2-bromo-4'-butylacetophenone,
2-bromo-4'-methoxyacetophenone,
2-bromo-4'-ethoxyacetophenone,
2-bromo-4'-propoxyacetophenone,
2 bromo-4'-butoxyacetophenone,
2-bromo-2'-chloroacetophenone,
2-bromo-2'-bromoacetophenone,
2-bromo-2'-fluoroacetophenone,
2-bromo-2'-methylacetophenone,
2-bromo-2'-ethylacetophenone,
2-bromo-2'-propylacetophenone,
2-bromo-2'-butylacetophenone,
2-bromo-2'-methoxyacetophenone,
2-bromo-2'-ethoxyacetophenone,
2-bromo-2'-propoxyacetophenone,
2-bromo-2'-butoxyacetophenone,
2-bromo-2'-chloro-3'-methoxyacetophenone,
2-bromo-2'-bromo-3'-methoxyacetophenone,
2-bromo-2'-fluoro-3'-methoxyacetophenone,
2-bromo-3'-methoxy-2'-methylacetophenone,
2-bromo-2',3'-dimethoxyacetophenone,
2-bromo-2'-ethoxy-3'-methoxyacetophenone,
2-bromo-2',3-dichloroacetophenone,
2-bromo-2'-bromo-3'-chloroacetophenone,
2-bromo-3'-chloro-2'-fluoroacetophenone,
2-bromo-3'-chloro-2'-fluoroacetophenone,
2-bromo-3'-chloro-2'-methylacetophenone,
2-bromo-3'-chloro-2'-methoxyacetophenone,
2-bromo-3'-chloro-2'-ethoxyacetophenone,
2-bromo-3'-bromo-4'-chloroacetophenone,
2-bromo-2',4'-dibromoacetophenone,
2-bromo-2'-bromo-4'-fluoroacetophenone,
2-bromo-2'-bromo-4'-methylacetophenone,
2-bromo-2'-bromo-4'-methoxyacetophenone,
2-bromo-4'-chloro-2'-fluoroacetophenone,
2-bromo-2',4'-difluoroacetophenone,
2-bromo-4'-bromo-2'-fluoroacetophenone,
2-bromo-2'-fluoro-4'-methylacetophenone,
2-bromo-2'-fluoro-4'-methoxyacetophenone,
2-bromo-4'-ethoxy-2'-fluoroacetophenone,
2-bromo-4'-chloro-2'-ethoxyacetophenone,
2-bromo-4'-bromo-2'-ethoxyacetophenone,
2-bromo-4'-fluoro-2'-ethoxyacetophenone,
2-bromo-4'-methyl-2'-ethoxyacetophenone,
2-bromo-4'-methoxy-2'-ethoxyacetophenone,
2-bromo-4',2'-diethoxyacetophenone,
2-bromo-4'-chloro-3'-ethoxyacetophenone,
2-bromo-4'-bromo-3'-ethoxyacetophenone,
2-bromo-4'-fluoro-3'-ethoxyacetophenone,
2-bromo-3'-ethoxy-4'-methylacetophenone,
2-bromo-3'-ethoxy-4'-methoxyacetophenone,
2-bromo-3',4'-diethoxyacetophenone,
2-bromo-5'-bromo-3'-chloroacetophenone,
2-bromo-3',5'-dibromoacetophenone,
2-bromo-5'-bromo-3'-fluoroacetophenone,
2-bromo-5'-bromo-3'-methylacetophenone,
2-bromo-5'-bromo-3'-methoxyacetophenone,
2-bromo-5'-bromo-3'-ethoxyacetophenone,
2-bromo-3'-chloro-5'-ethoxyacetophenone,
2-bromo-3'-bromo-5'-ethoxyacetophenone,
2-bromo-5'-ethoxy-3'-fluoroacetophenone,
2-bromo-5'-ethoxy-3'-methylacetophenone,
2-bromo-5'-ethoxy-3'-methoxyacetophenone,
2-bromo-3',5'-dimethoxyacetophenone,
2-bromo-3',5'-diethoxyacetophenone,
2-bromo-3',5'-dichloroacetophenone,
2-bromo-3',5'-difluoroacetophenone,
2-bromo-2',6'- dichloroacetophenone,
2-bromo-2',4',6'-trichloroacetophenone,
2-bromo-3',4',5'-trichloroacetophenone, etc.

After the completion of the reduction reaction, for example, the borane compound is decomposed by adding an acid (e.g. hydrochloric acid, etc.) to the reaction mass, and the solvent is optionally distilled off. Then, an extraction solvent (e.g. toluene, etc.) and an aqueous solution of an acid (e.g. hydrochloric acid, etc.) are added to the mass to remove an acid salt of optically active β-amino alcohols (5) to an aqueous layer, and then the solvent of the organic layer separated is distilled off to isolate the objective optically active carbinols. In addition, optically active β-amino alcohols (5) can be recovered by alkalifying the aqueous layer obtained, extracting it with an solvent (e.g. toluene, etc.) and then distilling off the solvent.

The optically active carbinols thus obtained can be further purified by subjecting to purification means such as distillation, various chromatographies, etc.

According to the present invention, there can be produced optically active carbinols which are useful as intermediates of drugs (e.g. remedy for obesity, remedy for diabetes, etc.)

and pesticides in high optical purity, even when using a metal boron hydride, which is less expensive and easily available industrially, as the hydrogen resource.

EXAMPLES

The following Examples further illustrate the present invention in detail, but are not to be construed to limit the scope thereof.

Reference Example 1

3'-Chloroacetophenone (154.6 g) and anhydrous methanol (dried with a molecular sieves 4A) (310 ml) were charged in a flask, and bromine (158.2 g) was added dropwise under stirring at 30° to 45° C. over one hour. After continuous stirring at the same temperature for 10 minutes, water (160 g) was added and the mixture was stirred continuously for one hour.

After cooling to −10° C., the crystal deposited was filtered to give 250 g of a solid. This solid was dissolved in heptane (750 g), and the resulting solution was washed twice with water (200 g), dried over anhydrous magnesium sulfate and filtered. Then, the filtrate was cooled to −30° C. and the crystal was filtered and dried to give 212.5 g of 2-bromo-3'-chloroacetophenone. It was analyzed by subjecting to gas chromatography. As a result, impurities were not observed, yield 91%.

Example 1

After a shrink tube was subjected to nitrogen substitution, (1S,2R)-(+)-norephedrine (0.032 g) and dried tetrahydrofuran (THF, dried using molecular sieves 4A) (1 ml) were charged in the shrink tube. Then, a 1M solution of THF-BH$^3$ (4.5 ml) was added under stirring, and the mixture was heated to 45° C. and stirred continuously at the same temperature for 90 minutes.

Then, a solution of 2-bromo-3'-chloroacetophenone (1 g) obtained above and dried THF (20 ml) was added dropwise at the same temperature over 175 minutes, followed by continuous stirring at the same temperature for 20 minutes. After cooling to 10° C., a 1M solution of hydrochloric acid (0.5 ml) obtained by diluting concentrated hydrochloric acid with ethanol was added slowly in order not to foam.

After the solvent was distilled off under reduced pressure, toluene (200 ml) and 7% hydrochloric acid (20 ml) were added to separate the aqueous and organic layers. The organic layer was washed with 7% hydrochloric acid (20 ml) and then with water (20 ml), dried over anhydrous magnesium sulfate and filtered. The solvent was distilled off to give 0.97 g of (R)-bromomethyl-3'-chlorophenyl carbinol, yield 96%.

The optical purity was determined by subjecting to liquid chromatography using an optically active column. As a result, it was 91% ee.

Example 2

According to the same manner as that described in Example 1 except for using (1R,2S)-(−)-norephedrine (0.032 g) in place of (1S,2R)-(+)-norephedrine, 0.95 g of (S)-bromomethyl-3'-chlorophenyl carbinol was obtained. The yield was 94.2% and the optical purity was 91% ee.

Example 3

According to the same manner as that described in Example 1 except for (i) using (1S,2R)-(+)-norephedrine (0.016 g) and a 1M solution of THF-BH$^3$(4.4 ml), (ii) using 2-bromo-4'-chloroacetophenone (1 g) in place of 2-bromo-3'-chloroacetophenone, and (iii) adding dropwise a solution of 2-bromo-4'-chloroacetophenone and THF over 400 minutes, 0.95 g of (R)-bromomethyl-4'-chlorophenyl carbinol was obtained. The yield was 94.2% and the optical purity was 94% ee.

Examples 4 to 6

According to the same manner as that described in Example 1 except for changing the substrate [halomethyl phenyl ketones (2)] and optically active amino alcohols [α-phenyl-substituted-β-amino alcohols(3)], optically active halomethyl phenyl carbinols (1) were obtained, respectively. The results are shown in Table 1.

Example 7

According to the same manner as that described in Example 1 except for using (i) 2-bromoacetophenone (1 mmol, 0.199 g) in place of 2-bromo-3'-chloroacetophenone, (ii) (1S,2R)-norephedrine (0.2 mmol, 0.03 g), and (iii) 1M solution of THF-BH$_3$ (2.2 ml, 2.2 mmol), an optically active carbinol was obtained. The results are shown in Table 1.

Examples 8 to 9

According to the same manner as that described in Example 7 except for using (i) (1S,2R)-2-amino-1-(2,5-dimethoxy)-1-propanol or (1 S,2R)-2-amino-1-(2,5-dimethyl)-1-propanol (0.05 mmol each) in place of (1S, 2R)-norephedrine and (ii) 1M solution of THF-BH$_3$ (1.05 ml, 1.05 mmol), optically active carbinols were obtained, respectively. The results are shown in Table 1.

Examples 10 to 11

According to the same manner as that described in Example 7 except for using (i) 2-chloroacetophenone (1 mmol, 0.155 g) in place of 2-bromoacetophenone, (ii) 95% borane dimethyl sulfide complex (2 mmol, 0.2 ml) in place of the 1M solution of THF-BH$_3$, and (iii) (1S,2R)-norephedrine (0.1 mmol, 0.015 g in Example 10) or (0.01 mmol, 0.0015 g in Example 11), optically active carbinols were obtained,. The results are shown in Table 1.

TABLE 1

| Example No. | Substrate (2) | Optically active amino alcohol (3) | Optical purity % ee |
| --- | --- | --- | --- |
| 4 | 2-Bromo-4'-methoxy-acetophenone | (1S, 2R)-norephedrine | 80 (R) |
| 5 | 2-Bromo-3'-methoxy-acetophenone | (1S, 2R)-norephedrine | 76 (R) |
| 6 | 2-Chloro-4'-chloro-acetophenone | (1S, 2R)-norephedrine | 78 (R) |
| 7 | 2-Bromo-acetophenone | (1S, 2R)-norephedrine | 85 (R) |
| 8 | 2-Bromo acetophenone | (1S, 2R)-2-amino-1-(2,5-dimethoxyphenyl)-1-propanol | 81 (R) |
| 9 | 2-Bromo acetophenone | (1S, 2R)-2-amino-1-(2,5-dimethylphenyl)-1-propanol | 74 (R) |
| 10 | 2-Chloro-acetophenone | (1S, 2R)-norephedrine | 82 (R) |
| 11 | 2-Chloro-acetophenone | (1S, 2R)-norephedrine | 79 (R) |

Example 12

After a shrink tube was subjected to nitrogen substitution, (R)-valinol (0.853 mmol, 0.088 g) and dried tetrahydrofuran (THF) (20 ml) were charged in the shrink tube. Then, a 1M solution of THF-BH$^3$ (9.4 mmol, 9.4 ml) was added under stirring, and the mixture was heated to 45° to 50° C. and stirred continuously at the same temperature for 90 minutes.

Then, a solution of 2-bromo-3'-chloroacetophenone (4.28 mmol, 1 g) obtained above and dried THF (20 ml) was added dropwise at the same temperature over 90 minutes, followed by continuous stirring at the same temperature for 10 minutes. After cooling to 10° C., a 1M solution of hydrochloric acid (2 ml) obtained by diluting concentrated hydrochloric acid with ethanol was added slowly in order not to foam.

After the solvent was distilled off under reduced pressure, toluene (190 g) and 7% hydrochloric acid (20 g) were added to separate the aqueous and organic layers. The organic layer was washed with 7% hydrochloric acid (20 g) and then with water (20 g), dried over anhydrous magnesium sulfate and filtered. The solvent was distilled off to give 0.93 g of (R)-bromomethyl-3'-chlorophenyl carbinol, yield 93%.

The optical purity was determined by subjecting to liquid chromatography using an optically active column. As a result, it was 89% ee.

Example 13

According to the same manner as that described in Example 12 except for using (S)-leucinol (0.853 mmol, 0.1 g) in place of (R)-valinol, 0.94 g of (S)-bromomethyl-3'-chlorophenyl carbinol was obtained.

The yield was 94% and the optical purity was 92% ee.

Examples 14 to 24

According to the same manner as that described in Example 12 changing the substrate [halomethyl phenyl ketones (2)] and optically active amino alcohols [optically active α-nonsubstituted-β-amino alcohols (4)], optically active halomethyl phenyl carbinols (1) were obtained. The results are shown in Table 2.

TABLE 2

| Example No. | Substrate (2) | Optically active Amino alcohol (4) | Optical purity % ee |
|---|---|---|---|
| 14 | 2-Bromoacetophenone | (R)-valinol | 96 (R) |
| 15 | 2-Bromoacetophenone | (S)-leucinol | 90 (S) |
| 16 | 2-Bromoacetophenone | (R)-phenylglycinol | 90 (R) |
| 17 | 2-Bromoacetophenone | (S)-phenylalaninol | 84 (S) |
| 18 | 2-Bromoacetophenone | (R)-alaninol | 85 (R) |
| 19 | 2-Bromoacetophenone | (S)-pyrrolinol | 91 (S) |
| 20 | 2-Bromo-4'-methoxy-acetophenone | (R)-phenylglycinol | 88 (R) |
| 21 | 2-Bromo-3'-methoxy-acetophenone | (R)-phenylglycinol | 88 (R) |
| 22 | 2-Chloro-2'-4'-di-chloroacetophenone | (S)-leucinol | 51 (S) |
| 23 | 2-Chloro-4'-chloro-acetophenone | (S)-valinol | 94 (S) |
| 24 | 2-Bromo-4'-methyl acetophenone | (S)-leucinol | 81 (S) |

Example 25

To a mixture of tetrahydrofuran (30 ml) and sodium boron hydride (8.56 mmol, 0.334 g), dimethylsulfuric acid (8.56 mmol, 1.102 g) was added at 40° C. under a nitrogen flow, and the mixture was stirred continuously while maintaining at 45° to 50° C. for one hour.

Then, a solution of (1S,2R)-norephedrine (0.856 mmol, 0.1294 g) and tetrahydrofuran (2 ml) was added at the same temperature, followed by continuous stirring at the same temperature for 1.5 hours. Then, a solution of 2-bromo-3'-chloroacetophenone (4.28 mmol, 1 g) and tetrahydrofuran (20 ml) was added dropwise over 30 minutes, and the mixture was stirred continuously while maintaining at the same temperature for 0.5 hours.

After the completion of the reaction, the reaction solution was cooled to 10° C. and a hydrochloric acid/methanol solution (concentrated hydrochloric acid was diluted with methanol to prepare a 1N solution) (85 ml) was added. After stirring one hour, the solvent was distilled off and toluene (200 ml) and 7% hydrochloric acid (50 ml) were added to carry out extraction. The organic layer was washed with aqueous sodium bicarbonate and then with water and dried over magnesium sulfate, and then the solvent was distilled off to give 0.91 g of (R)-3'-chlorophenylbromomethyl carbinol. The optical purity was 84.6% ee.

Examples 26 to 29

According to the same manner as that described in Example 25 except for using 4'-phenylacetophenone (4.28 mmol, 0.84 g), 3',4'-methylenedioxyacetophenone (4.28 mmol, 0.703 g), 3-chloropropyl-p-t-butylphenylketone (4.28 mmol, 1.02 g) or 2',4'-dichloroacetophenone (4.28 mmol, 0.809 g) in place of 2-bromo-3'-chloroacetophenone, respective optically active carbinols (9) were obtained. The results are shown in Table 3.

TABLE 3

| Example No. | Optically active carbinol (9) | Optical yield % ee |
|---|---|---|
| 26 | (S)-4'-phenylphenylmethyl carbinol | 80 |
| 27 | (S)-3',4'-methylenedioxymethyl carbinol | 74 |
| 28 | (R)-3-chloropropyl-p-t-butylphenyl-carbinol | 72 |
| 29 | (S)-2',4'-dichlorophenylmethyl carbinol | 61 |

Examples 30 to 34

According to the same manner as that described in Example 25 except for using (S)-leucinol (0.856 mmol, 0.1 g), (R)-phenylglycinol (0.856 mmol, 0.117 g), (1S,2R)-2-amino-1,2-diphenylethanol (0.856 mmol, 0.183 g), (S)-valinol (0.856 mmol, 0.088 g) or (R)-5,5-diphenyl-2-methyl-3,4-propane-1,3,2-oxazaboridine (0.856 mmol, 0.237 g) in place of (1S,2R)-norephedrine, optically active carbinols (9) were obtained. The results are shown in Table 4.

TABLE 4

| Example No. | Optically active amino alcohols (5) | Optical yield % ee |
|---|---|---|
| 30 | (S)-leucinol | 72 (S) |
| 31 | (R)-phenylglycinol | 71 (R) |
| 32 | (1S, 2R)-2-amino-1,2-diphenyl ethanol | 91 (R) |
| 33 | (S)-valinol | 90 (S) |
| 34 | (R)-5,5-diphenyl-2-methyl-3,4-propane-1,3,2-oxazaboridine | 87 (R) |

Examples 35 to 37

According to the same manner as that described in Example 25 except for using (R)-phenylglycinol (0.856 mmol, 0.117 g) and acetophenone (4.28 mmol, 0.514 g) in Example 35, (1S,2R)-2-amino-1,2-diphenylethanol (0.856 mmol, 0.183 g) and 2-bromo-3'-methoxyacetophenone (4.28 mmol, 0.98 g) in Example 36 or (S)-valinol (0.856 mmol, 0.088 g) and 2-chloro-4'-chloroacetophenone (4.28 mmol, 0.809 g) in Example 37 in place of (1S,2R)-norephedrine and 2-bromo-3'-chloroacetophenone, optically active carbinols (9) were obtained. The results are shown in Table 5.

TABLE 5

| Example No. | Optically active carbinol (9) | Optical yield % ee |
|---|---|---|
| 35 | (S)-phenylmethyl carbinol | 96 |
| 36 | (S)-3'-methoxyphenylbromomethyl carbinol | 86 |
| 37 | (S)-4'-chlorophenylmethyl carbinol | 83 |

Example 38

To a mixture of tetrahydrofuran (10 ml), sodium boron hydride (10 mmol, 0.378 g) and (1S,2R)-norephedrine (1 mmol, 0.151 g), a boron trifluoride-diethyl ether complex (1.5 mmol, 0.18 ml) was added with stirring under a nitrogen flow, and the mixture was stirred continuously at 60° C. for one hour. After cooling to room temperature, a boron trifluoride-diethyl ether complex (11.8 mmol, 1.45 ml) was added, followed by heating to 60° C. over one hour.

Then, a solution of 2-bromoacetophenone (10 mmol, 1.991 g) and tetrahydrofuran (5 ml) was added dropwise at the same temperature for 10 minutes, followed by continuous stirring at the same temperature for 10 minutes.

After the completion of the reaction, 10% hydrochloric acid (10 ml) was added under ice cooling, followed by stirring. Then, the reaction solution was extracted with toluene and the organic layer was washed with water to give a toluene solution of (R)-2-bromo-1-phenylethanol. The reaction rate was 100% and the optical purity was 79.8% ee.

Example 39

According to the same manner as that described in Example 38 except for using (1S,2R)-2-amino-1,2-diphenyl ethanol (1 mmol, 0.2133 g) in place of (1S,2R)-norephedrine, a toluene solution of (R)-2-bromo-1-phenylethanol was obtained.

The reaction rate was 100% and the optical purity was 87.4% ee.

We claim:

1. A process for producing optically active halomethyl phenyl carbinols of the formula (1)

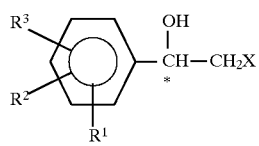

wherein X is a chlorine atom or bromine atom; $R^1$, $R^2$ and $R^3$ independently represent a hydrogen atom, halogen atom, a lower alkyl group or a lower alkoxy group; and * is an asymmetric carbon, comprising reducing halomethyl phenyl ketones of the formula (2):

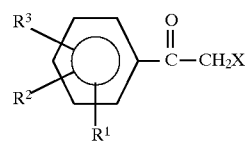

wherein X, $R^1$, $R^2$ and $R^3$ are as defined above, using an asymmetric reducing agent obtained from boranes and either optically active α-phenyl-substituted-β-amino alcohols of the formula (3):

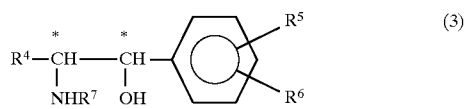

wherein $R^4$ represents an alkyl group having 1 to 6 carbon atoms; $R^5$ and $R^6$ independently represent a hydrogen atom, a lower alkyl group or a lower alkoxy group; $R^7$ represents a hydrogen atom, a lower alkyl group or an optionally substituted aralkyl group; and * is an asymmetric carbon, or optically active α-non-substituted-β-amino alcohols of the formula (4):

wherein $R^8$ represents an alkyl group having 1 to 6 carbon atoms, aryl group which is optionally substituted with a lower alkyl group or a lower alkoxy group, or an aralkyl group which is optionally substituted with a lower alkyl group or a lower alkoxy group; $R^9$ represents a hydrogen atom, a lower alkyl group or an optionally substituted aralkyl group, or $R^9$ and $R^8$ bond together to represent a lower alkylene group; and * is an asymmetric carbon.

2. The process according to claim 1, wherein the asymmetric reducing agent is obtained from boranes and optically active α-phenyl-substituted-β-amino alcohols of formula (3).

3. The process according to claim 1, wherein the asymmetric reducing agent is obtained from boranes and optically active α-nonsubstituted-β-amino alcohols of formula (4).

4. The process according to claim 2 or 3, wherein X of the halomethyl phenyl ketones of formula (2) is a bromine atom.

5. The process according to claim 4, wherein the halomethyl phenyl ketones of formula (2) are obtained by reacting methyl phenyl ketones of the formula (6):

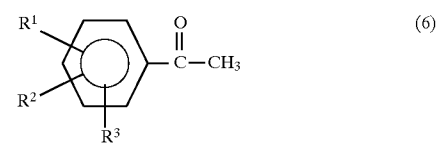

wherein $R^1$, $R^2$ and $R^3$ respectively indicate a hydrogen atom, a halogen atom, a lower alkyl group or a lower alkoxy group, with bromine in a methanol solvent.

6. The process according to claim 2, wherein optically active α-phenyl-substituted-β-amino alcohols of formula (3) are at least one member selected from the group consisting of optically active norephedrine, optically active 2-amino-1-(2,5-di-methylphenyl)-1-propanol, optically active 2-amino-1-(2,5-dimethoxyphenyl)-1-propanol and optically active 2-amino-1-(2,5-diethoxyphenyl)-1-propanol.

7. The process according to claim 3, wherein optically active α-nonsubstituted-β-amino alcohols of formula (4) are at least one member selected from the group consisting of optically active valinol, optically active leucinol, optically active alaninol, optically active phenylalaninol, optically active phenylglycinol and optically active prolinol.

8. The process according to claim 1, wherein the asymmetric reducing agent is an asymmetric reducing agent prepared by using optically active α-phenyl-substituted-β-amino alcohols of formula (3) or optically active α-nonsubstituted-β-amino alcohols of formula (4) in an amount of 0.01 to 1 mole per one mole of the halomethyl phenyl ketones of formula (2).

9. The process according to claim 1, wherein the boranes are at least one member selected from the group consisting of diborane, tetraborane, hexaborane, tetrahydrofuranborane complex, dimethyl sulfide-borane complex, alkyl borane, catechol borane and thioxaneborane.

10. The process according to claim 1, wherein the asymmetric reducing agent is the one prepared by using boranes in a n amount of 0.8 to 2 mole (in terms of boron) per one mole of optically active α-phenyl -substituted-β-amino alcohols of formula (3) or of optically active α-nonsubstituted-β-amino alcohols of formula (4).

11. The process according to claim 1, wherein the asymmetric reducing agent is the one prepared by using boranes in an amount of 0.3 to 2 mole (in terms of boron) per one mole of halomethyl phenyl ketones of formula (2).

12. The process according to claim 1, wherein $R^1$, $R^2$ and $R^3$ are fluorine, chlorine, bromine, methyl, ethyl, n-propyl, i-propyl, n-butyl, i-butyl, sec-butyl, t-butyl, methoxy, ethoxy, propoxy, and butoxy.

13. The process according to claim 2, wherein $R^4$ is selected from the group consisting of methyl, ethyl, n-propyl, i-propyl, n-butyl, i-butyl, sec-butyl, t-butyl, pentyl, hexyl, and cyclohexyl; wherein $R^5$ and $R^6$ are independently selected from the group consisting of methyl, ethyl, n-propyl, i-propyl, n-butyl, i-butyl, sec-butyl, t-butyl, methoxy, ethoxy, propoxy, and butoxy; and wherein $R^7$ is selected from the group consisting of methyl, ethyl, n-propyl, i-propyl, n-butyl, i-butyl, sec-butyl, t-butyl, and optionally substituted aralkyl groups selected from benzyl, phenylethyl, and p-methylbenzyl, wherein the aralkyl group is optionally substituted with $C_1$–$C_4$ alkyl, halogen or $C_1$–$C_4$ alkoxy.

14. The process according to claim 3, wherein $R^8$ is selected from the group consisting of methyl, ethyl, n-propyl, i-propyl, n-butyl, i-butyl, sec-butyl, t-butyl, pentyl, hexyl; optionally substituted aryl groups selected from phenyl, naphthyl, p-methylphenyl, and p-methoxyphenyl, wherein the aryl groups are optionally substituted with $C_1$–$C_4$ alkyl or $C_1$–$C_4$ alkoxy; and optionally substituted aralkyl groups selected from benzyl, phenylethyl, p-methylbenzyl, and p-groups selected from benzyl, phenylethyl, p-methylbenzyl, and p-methoxybenzyl, wherein the aralkyl groups are optionally substituted with $C_1$–$C_4$ alkyl or $C_1$–$C_4$ alkoxy; and wherein $R^9$ is selected from the group consisting of hydrogen, methyl, ethyl, n-propyl, i-propyl, n-butyl, i-butyl, sec-butyl, t-butyl; optionally substituted aralkyl groups selected from benzyl, phenylethyl, p-methylbenzyl, and p-methoxybenzyl, wherein the aralkyl groups are optionally substituted with $C_1$–$C_4$ alkyl or $C_1$–$C_4$ alkoxy.

15. The process according to claim 3, wherein $R^8$ and $R^9$ are bonded together to form a lower alkylene group selected from the group consisting of methylene, dimethylene, trimethylene, and tetramethylene.

* * * * *